United States Patent [19]

Johnson

[11] Patent Number: 4,921,675
[45] Date of Patent: May 1, 1990

[54] BIOCIDAL GAS STERILIZER

[75] Inventor: Kenneth A. Johnson, Wayne, N.Y.

[73] Assignee: MDT Corporation, Rochester, N.Y.

[21] Appl. No.: 43,610

[22] Filed: Apr. 28, 1987

[51] Int. Cl.$^5$ .......................... A61L 2/20; A61L 2/24
[52] U.S. Cl. ...................................... 422/34; 422/28;
422/34; 422/111; 422/117; 422/292; 422/295
[58] Field of Search ................... 422/34, 28, 110, 111,
422/292, 295, 117

[56] References Cited

U.S. PATENT DOCUMENTS

| | | |
|---|---|---|
| 2,891,838 | 6/1959 | Kaye . |
| 2,965,936 | 12/1960 | Kaye . |
| 3,035,886 | 5/1962 | Hickey . |
| 3,068,064 | 12/1962 | McDonald . |
| 3,163,494 | 12/1964 | Kaye . |
| 3,258,312 | 6/1966 | Olson . |
| 3,454,353 | 7/1969 | Bjork . |
| 3,490,863 | 1/1970 | Schumann et al. . |
| 3,564,861 | 2/1971 | Andersen et al. . |
| 3,944,387 | 3/1976 | Schreckendgust . |
| 4,067,691 | 1/1978 | McGady et al. . |
| 4,130,393 | 12/1978 | Fox . |
| 4,203,943 | 5/1980 | Gillis et al. . |
| 4,457,892 | 7/1984 | Young . |
| 4,576,918 | 7/1986 | Young . |

Primary Examiner—Robert J. Warden
Assistant Examiner—Jill Johnston
Attorney, Agent, or Firm—Trask, Britt & Rossa

[57] ABSTRACT

A method and apparatus for sterilizing materials and/or equipment by exposure to a biocidal gas. The apparatus is designed to be used with an exhaust vent system. A sensor is provided in the exhaust vent system for determining flow of gas therethrough. The sensor provides a signal to the control unit of the sterilizer so as to control the operational status of the sterilizing apparatus when a flow of gas in the exhaust vent system is stopped.

13 Claims, 2 Drawing Sheets

BIOCIDAL GAS STERILIZER

BACKGROUND OF THE INVENTION

This invention is directed to a method and apparatus for sterilizing various types of materials and/or equipment by exposure to biocidal gases such as ethylene oxide.

Ethylene oxide is widely used to sterilize a variety of products and materials. It may be used alone or in a mixture with dilutant gases such as Dichlorodifluoromethane or Carbon Dioxide. It is known that ethylene oxide exposure to humans presents a hazard as it may cause eye and skin irritation, is a human mutagen and a suspected carcinogen. In view of the potential hazards that an ethylene oxide sterilizer may present, these sterilizers are usually maintained in a room which is well ventilated so as to minimize exposure of humans to the gas. Typically an exhaust vent is provided for drawing air from the room in which the sterilizer is placed and venting that air to the atmosphere. In some systems a warning light or some other type of indicator, which operates independently of the sterilizer, is provided to warn the operator that the exhaust vent is not operating. However, there still exists the possibility that the exhaust vent will not be turned on or the exhaust vent may become nonoperational during operation of the sterilizing apparatus. This could result in an excess amount of ethylene oxide being present in the room.

Applicant has invented a method and apparatus whereby the risk of exposure to ethylene oxide or other biocidal gas is minimized when and if the exhaust vent becomes inoperative.

SUMMARY OF THE INVENTION

In one aspect of the present invention there is provided a biocidal gas sterilizer for use with an exhaust vent system. The sterilizer comprises a main sterilizing chamber having an access door, means for introducing a biocidal gas into the sterilizer and exhaust means for removing biocidal gas from the sterilizing chamber. Monitoring means is provided for monitoring the operation of the exhaust vent system. Means are also provided for preventing operation of the sterilizer when the exhaust vent system is not operational.

In another aspect of the present invention there is provided a method of sterilizing articles using a biological gas sterilizing apparatus having a sterilizing chamber, an access door to the chamber, means for introducing biocidal gas into the chamber and exhaust means for removing biocidal gas from the sterilizing chamber. An exhaust vent system is connected to the sterilizing apparatus for evacuating biocidal gas therefrom. Monitoring means is also provided for monitoring the status of the exhaust vent system. The method includes the steps of monitoring the operational status of the exhaust vent system and preventing operation of the sterilizer when the monitoring means senses that the operational status of the exhaust vent system is off.

In yet another aspect of the present invention there is provided a system for sterilizing articles using the biocidal gas comprising a sterilizing apparatus having a main sterilization chamber, means for introducing biocidal gas into the chamber and exhaust means for removing biocidal gas from sterilizing the chamber; an exhaust vent system for evacuating biocidal gas from the sterilizer; monitoring means for monitoring the operational status of said vent means; and means for preventing operation of said sterilizer when said exhaust vent system is in the nonoperational mode.

DETAILED DESCRIPTION OF THE ILLUSTRATED EMBODIMENT

Figure 1:
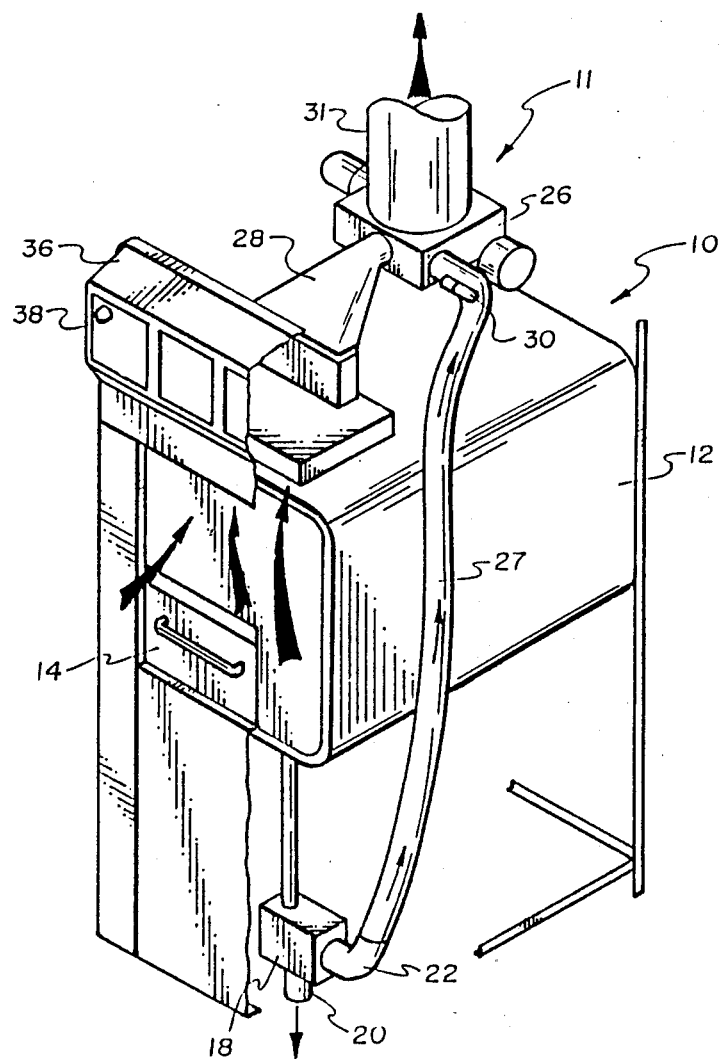
FIG. 1 is a perspective view partially broken away of a sterilizing apparatus and exhaust system made in accordance with the present invention.
Figure 2:
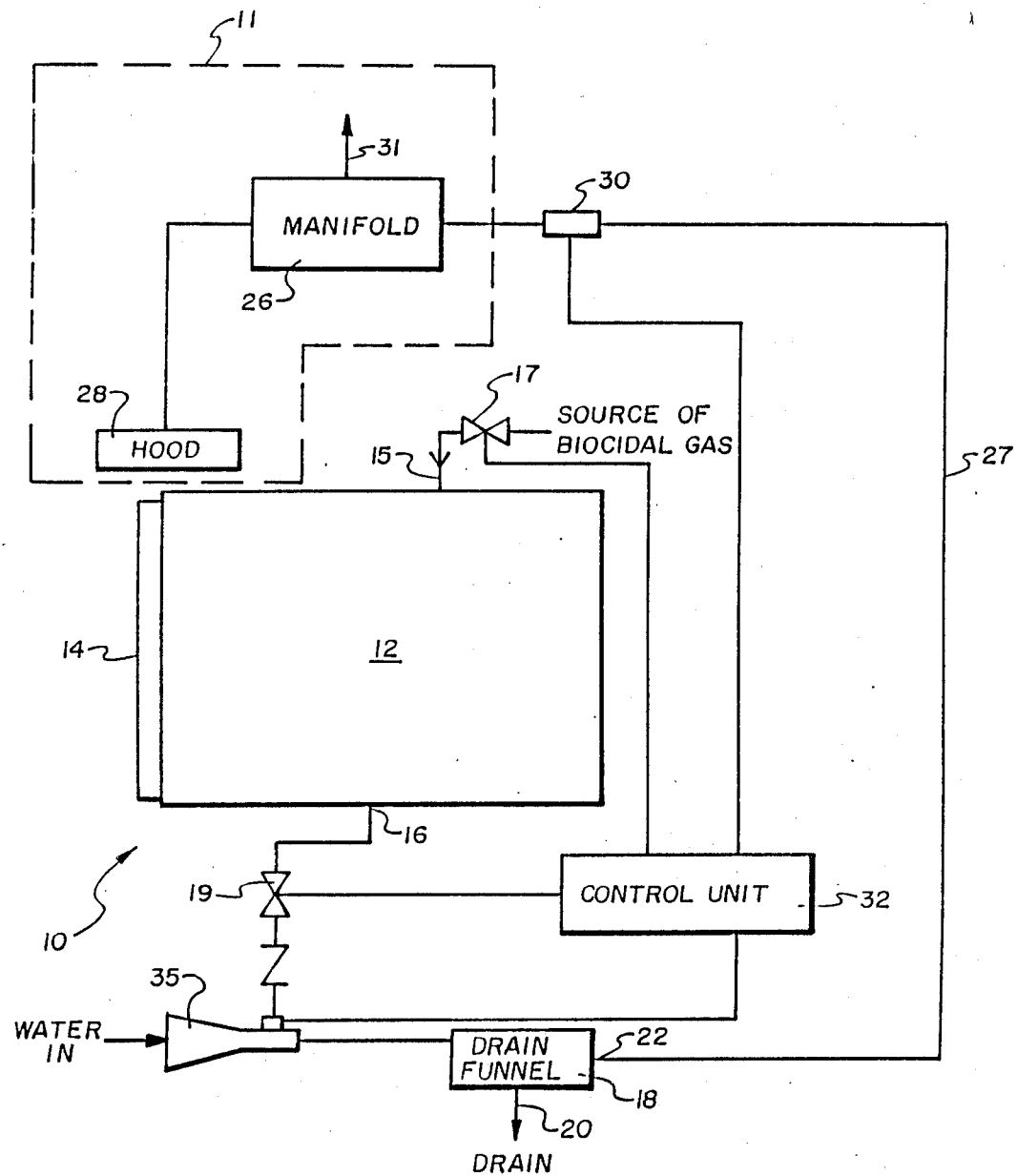
FIG. 2 is a diagrammatic representation of an apparatus and exhaust system made in accordance with the present invention.

Referring to FIGS. 1 and 2 there is illustrated a system made in accordance with the present invention for sterilizing a variety of articles. The system comprises a sterilizing apparatus 10 and exhaust system 11 (indicated by dash lines in FIG. 2).

The apparatus 10 comprises a sterilization chamber 12 wherein the desired material and or equipment is placed for sterilization. The sterilization chamber 12 is provided with a door 14 which in the present embodiment is slideably mounted to apparatus 10. However, it is clear that the present invention is not limited to the particular size and shape chamber or type door as illustrated. Various modifications may be made as is well known in the art. The sterilization chamber 12 is capable of receiving ethylene oxide gas and/or biocidal gas mixtures in a normal conventional manner as presently done by prior art sterilizers. In the particular embodiment illustrated an ethylene oxide gas mixture is provided from an external source to the sterilizing chamber 12 through inlet 15 and valve 17 to sterilizing chamber 12. It is to be understood that the present invention is also applicable to sterilizers which use other biocidal gases, for example but not by way of limitation, formaldehyde, chlorine dioxide. Sterilizing chamber 12 has an outlet 16 which is connected to a drain funnel 18 which has an outlet 20 for discharging condensate to drain. An outlet valve 19 is positioned in the passage connecting outlet 16 to drain funnel 18 for controlling the exhausting of chamber 12. A second outlet 22 is provided in drain funnel 18 whereby excess air and gas is drawn therefrom by exhaust vent system 11 through manifold 26 and passageway 27. Exhaust vent system 11 is separate from apparatus 10 and is provided in the room in which the apparatus 10 is placed, however, portions of exhaust vent system 11 may be supplied as part of apparatus 10. Typically manifold 26 is connected to the outside atmosphere by the building exhaust system through passageway 31 which is powered by a fan (not shown) located outside of the building which provides a negative pressure within the exhaust vent system 11. However, if desired, exhaust vent system 11 may be connected directly to atmosphere and may include a fan in the general area of manifold 26.

Exhaust vent system 11 is further provided with an exhaust hood 28 which is placed over the door opening so as to continuously draw off air from around the door seal as indicated by the arrows. This air is then funneled to exhaust vent system 11 through manifold 26. Exhaust hood 28 may be mounted to the ceiling or the apparatus 10 as desired. In the particular embodiment illustrated exhaust hood 28 is mounted to apparatus 10.

An exhaust vent flow switch 30 is placed in passageway 27 for monitoring of whether a gas (including air) is flowing therethrough. This monitors whether gas is flowing through exhaust vent system 11. In the particular embodiment illustrated the exhaust flow switch 30 is placed in passageway 27, however, the exhaust flow switch 30 may be placed at any convenient point in the exhaust vent system 11 or passageways thereto. All that is necessary is that the exhaust flow switch 30 be placed at a point that monitors the flow of gas through the exhaust vent system 11 which in turn identifies the operational status thereof. In the particular embodiment illustrated the exhaust vent flow switch 30 is a vane switch. The output of exhaust vent flow switch 30 is connected to a microprocessor control unit 32 used to control the apparatus 10. The microprocessor control unit 32 is programmed to monitor the flow of a gas and/or air through exhaust vent system 11.

The apparatus 10 is provided with internal exhaust means for removing ethylene oxide from the chamber 12 as is normally done in ethylene oxide sterilizers of the prior art. Typically, a vacuum is applied to the outlet 16 which draws ethylene oxide from the chamber 12 to drain funnel 18. In the particular embodiment illustrated a water ejector 35 is used to provide a vacuum, however, any other desired means may be used to provide a vacuum.

The control panel 36 is provided with indicating means for displaying the operational status of the exhaust vent system 11. In the particular embodiment illustrated, indicating means comprises a warning light 38. In the particular embodiment illustrated an additional audible alarm is also provided.

The operation of the apparatus 10 will now be discussed in detail. When the apparatus 10 is initially turned on, warning light 38 on control panel 36 will advise the operator as to whether or not a gas is flowing through exhaust vent system 11. If warning light 38 is on, this indicates that the vent system 11 is not operating. The chamber 12 is then filled with the appropriate items to be sterilized and the door 14 closed. The desired exposure time to ethylene oxide is programmed in apparatus 10 as is normally done in the prior art. The apparatus 10 may be operated up until the point at which ethylene oxide is to be introduced in the chamber. If at this point the control unit 32 of apparatus 10 senses that the exhaust vent system 11 is not operational, ethylene oxide will not be allowed to enter chamber 12. In the particular embodiment illustrated this is accomplished by preventing the opening of valve 17. If the exhaust vent flow switch 30 senses that airflow is being provided ethylene oxide gas will be allowed to fill the chamber 26 until the appropriate charge is received. If, during the introducing of ethylene oxide a flow of gas is not sensed by exhaust vent flow switch 30 ethylene oxide gas will be allowed to continue entering chamber 12 to completion, however, warning light 38 will be activated to indicate that a flow of gas is not present in exhaust vent system 11. After the chamber 12 is filled with ethylene oxide, the exposure phase will start. The exposure phase for the purpose of this invention is that time period during which the items within the sterilizer are exposed to ethylene oxide or other biocidal gas for sterilization. Once the exposure phase begins, if a loss of airflow through exhaust vent system 11 is sensed, warning light 38 will light up on control panel 36. However, the exposure phase will continue up until the end of the exposure phase. After completion of the exposure phase, if the exhaust vent system 11 is operational, the apparatus 12 will go into aeration cycle whereby ethylene oxide is removed from chamber 12. For the purpose of this invention, the aeration cycle shall mean that time period which ethylene oxide is first evacuated from the chamber 12 and that time period which a vacuum is applied to the chamber to remove ethylene oxide from the load. As is normally done in the prior art, the excess condensate is discharged through drain funnel 18. If during this aeration phase the exhaust flow switch 30 senses that a flow of gas is not present, the microprocessor control unit 32 will stop the exhausting of chamber 12 closing valve 19. Warning light 38 on control panel 36 will be activated. The aeration phase will resume only after the flow through exhaust vent system 11 is resumed and sensed by exhaust flow switch 30. Optionally, as is incorporated in the embodiment illustrated, an audible alarm will be activated, in addition to the warning light 38, if exhaust vent system 11 is not operational during the introduction of the biocidal gas, exposure or aeration phase. After the aeration phase has been completed loss of airflow through exhaust vent system 11 will only activate warning light 38.

It can be seen that if, for any reason, the flow of gas through exhaust vent system 11 ceases prior to the introduction of the ethylene oxide into the sterilization chamber 12 or during the aeration cycle, the apparatus 10 will stop thereby preventing the introduction of ethylene oxide into chamber 12 or further exhausting of ethylene oxide from chamber 12. The apparatus 10 will only continue upon reactivation of the exhaust vent system 11. An override may, of course, be provided for the repair of the system or other purpose that may be required. However, during normal operation of the apparatus 10 means are provided for minimizing the potential exposure of a hazardous biocidal gas. Additionally, any leakage that may occur around the door is minimized. Operation of the exhaust vent system 11 also draws out residual ethylene oxide or biocidal gas from chamber 12 when the door is opened for removal of the sterilized items following the exposure and aeration phase.

The present invention provides positive means for controlling operation of the sterilizing apparatus in response to the operational status of the exhaust vent system so as to minimize the possibility of introducing a hazardous gas in the surrounding area.

Various modifications may be made without departing from the scope of the present invention, for example, but not by way of limitation, the biocidal gas may be introduced by means of a cartridge placed within the chamber 12, various other biocidal gases may be used other than those disclosed herein and various other functions of the sterilizer may be controlled in response to the airflow within the exhaust vent system.

What is claimed is:

1. A system for sterilizing articles with a biocidal gas, comprising:
   a sterilizing apparatus situated within an enclosed working space and including a sterilization chamber, gas supply means for introducing biocidal gas into said sterilization chamber and exhaust means for removing biocidal gas from said sterilization chamber;
   a venting system, operably associated with said sterilizing apparatus for evacuating gas from said working space, including from said exhaust means, said venting system including means for introducing the flow of gas therethrough from within to outside said working space;

monitoring means operably associated with the venting system for detecting the flow of gas through said venting system; and control means, responsive to said monitoring means, to prevent the operation of either said gas supply means or said exhaust means, except when gas is detected to be flowing through said venting system.

2. A system according to claim 1 wherein said monitoring means comprises a vane switch operable in response to the flow of gas through said venting system.

3. A system according to claim 1 further comprising means for displaying the operational status of said venting system in response to said monitoring means.

4. A system according to claim 1 further comprising means for audibly indicating the operational status of said venting system.

5. A system according to claim 1 wherein said control means is operable to effect a sterilization cycle including a biocidal gas introduction phase, a subsequent exposure phase and thereafter, an exhaust phase; and is further operable in response to the detection by said monitoring means of the absence of gas flow in said venting means at the commencement of said introduction phase to abort said sterilization cycle, but in response to the detection by said monitoring means of gas flow in said venting means during the entirety of said introduction phase, to permit said sterilization cycle to proceed during the entirety of said exposure phase.

6. A system according to claim 1 wherein said gas supply means for introducing biocidal gas comprises valve means which controls the flow of said biocidal gas from a source of biocidal gas into said chamber.

7. A system according to claim 1 wherein said sterilizing chamber includes an access door, said system further including an exhaust hood positioned to draw air from around said door into said venting system.

8. A system according to claim 1 wherein the control means operates to shut off the sterilizer apparatus when said control means detects the absence of gas flow through said venting system prior to the introduction of biocidal gas into said sterilization chamber.

9. A sterilizing apparatus, comprising:

a sterilization chamber with a door capable of opening to permit access to the interior of said chamber and of closing to seal said chamber;

gas supply means for introducing biocidal gas to the interior of said chamber;

exhaust means for removing biocidal gas from said interior;

venting means capable of connection to an external vacuum system, constituting means for applying a vacuum to said exhaust means, thereby to induce the flow of gas through said venting means;

monitoring means operably associated with said venting means for detecting the flow of gas through said venting means; and control means, responsive to said monitoring means, to prevent the operation of said gas supply means except when gas is detected to be flowing through said venting means.

10. A sterilizing apparatus according to claim 9 wherein said control means is operably responsive to said monitoring means to prevent the operation of said exhaust means except when gas is detected to be flowing through said venting means.

11. A sterilizing apparatus according to claim 10 wherein said venting means includes an exhaust hood positioned above said door constituting means for drawing air from around the perimeter of said door when gas is flowing through said venting means.

12. A sterilizing apparatus according to claim 9 wherein said control means is operable to effect a sterilization cycle including a biocidal gas introduction phase, a subsequent exposure phase and thereafter, an exhaust phase, and is further operable in response to the detection by said monitoring means of the absence of gas flow in said venting means at the commencement of said introduction phase to abort said sterilization cycle.

13. A sterilization apparatus according to claim 12 wherein said control means is further operable, in response to the detection by said monitoring means of gas flow in said venting means during the entirety of said introduction phase, to permit said sterilization cycle to proceed during the entirety of said exposure phase.

* * * * *